United States Patent [19]

Villax et al.

[11] 4,343,739

[45] Aug. 10, 1982

[54] PROCESS OF SELECTIVE SOLVOLYSIS

[75] Inventors: Ivan Villax, Lisbon; Philip R. Page, Parede, both of Portugal

[73] Assignee: Plurichemie Anstalt, Vaduz, Liechtenstein

[21] Appl. No.: 267,553

[22] Filed: May 27, 1981

[30] Foreign Application Priority Data

May 27, 1980 [PT] Portugal .................................. 71309

[51] Int. Cl.$^3$ ............................................... C07J 5/00
[52] U.S. Cl. ................................................ 260/397.45
[58] Field of Search ................................... 260/397.45

[56] References Cited

U.S. PATENT DOCUMENTS 4,024,131  5/1977  Villax ............................. 260/397.4

*Primary Examiner*—Elbert L. Roberts
*Attorney, Agent, or Firm*—Ostrolenk, Faber, Gerb & Soffen

[57] ABSTRACT

The 17α-monoesters and 17α,21-diesters of corticosteriods are well known and represent nowadays the most efficient group of anti-inflammatory compounds for topical application, having minimal systemic action.

9 Claims, No Drawings

PROCESS OF SELECTIVE SOLVOLYSIS

The present invention provides a new and efficient route for the preparation of 17α-mono- and 17α,21-diesters of 20-keto steroids with good yield and of high purity, comprising the selective solvolysis under anhydrous conditions at 21 of a 17α,21-diester yielding 17α-monoester, or an 11β-trifluoroacetate-17α,21-diester yielding 11β-trifluoroacetate-17α-monoester, followed by selective removal of the 11β-trifluoroacetate group, when present, by solvolysis under alkaline conditions yielding the 17α-monoesters.

A further object of the present invention is to solvolyse selectively the 11β-trifluoroacetate group of an 11β-trifluoroacetate-17α,21-diester in alkaline conditions to a 17α,21-diester, furthermore to solvolyse simultaneously at 11β- and 21- an 11β-trifluoroacetate-17α,21-orthodiester in alkaline media to yield the 17α-monoesters.

The acylation with a lower aliphatic carboxylic acid having up to 5 carbon atoms of the 17-hydroxy group of 17-hydroxy-20-keto-pregnanes was described by Huang-Minlon et al.: "Steroid 17(α)-acetates", Journal of the American Chemical Society, Vol. 74, pp. 5394–96 (1952), as well as in British Pat. No. 737,291, by treating a 17-hydroxy-20-keto-pregnane with an acid anhydride of a lower aliphatic acid, preferably in presence of a strong acid such as paratoluenesulphonic acid. The selective acid hydrolysis of 17α,21-diesters into 17-monoesters has been reported by R. M. Evans et al., in Journal of the Chemical Society (1956), p. 4359.

Belgian Pat. No. 618,831 (priority 1962) described for the first time the preparation of cyclic 17α,21-orthodiesters of corticosteroids having a 17α,21-dihydroxy 20-keto side chain, which are subsequently hydrolysed under acid conditions into 17α-acyl esters, as described in Belgian Pat. No. 619,180 (priority 1962). These two Belgian patents also refer to the high anti-inflammatory activity of the 17α-monoacylates and with special reference to their dermatological applicability.

British Pat. No. 1,047,518 (priority 1963) describes the preparation of a number analogous compounds to those described in Belgian Pat. Nos. 618,831 and 619,180, via acid hydrolysis of the cyclic 17α,21-orthodiesters or 17α,21-diesters, having 17α-ester groups of 2 to 6 carbon atoms. Additionally the aqueous perchloric acid hydrolysis of 17,21-diesters is described.

British Pat. No. 1,070,751 (priority 1964) describes 17-esters of 17-hydroxy-21-desoxy steroids by direct acylation of the 17α-hydroxy group with an acid anhydride or acid chloride in presence of a strong acid catalyst such as para-toluenesulphonic acid, the ester function containing up to 3 carbon atoms.

British Pat. No. 1,097,165 (priority 1965) describes a novel 17-acylating process by treating an 11β-trihaloacetate of a 17α-hydroxy-21-ester of 20-keto-pregnanes with an acylating medium consisting of a trihalo carboxylic anhydride, a strong acid catalyst such as para-toluenesulphonic acid and a carboxylic acid of 1 to 9 atoms, yielding 11β-trihaloacetate-17α,21-diesters. The selective protection of the 11-hydroxy group of steroids with trifluoroacetic anhydride therein employed has been first described in U.S. Pat. No. 2,800,489 (priority 1953).

British Pat. No. 1,097,164 (priority 1965) describes a selective solvolysis of 11β-trihaloacetate-17α,21-diesters in the presence of certain salts in a lower alcohol to yield 17α,21-diesters. Furthermore, concentrated aqueous perchloric acid hydrolysis is therein illustrated to prepare 17α-monoesters from 17α,21-diesters.

British Pat. No. 1,227,992 (priority 1968) describes a route similar to the one above but using 11β-trimethylsilyl protection and eliminating the 11β-ether group and then the 21-ester by acid hydrolysis.

U.S. Pat. No. 4,024,131 (priorities 1974 and 1975) prepares 17α-mono- and 11β,17α-diesters of 21-desoxy-20-keto steroids and 17α-monoesters, 17α,21-diesters and 11β,17α,21-triesters of 1 to 16 carbon atoms, via 11β-trihaloacetates or 11β-tetrahydropyran-(2'yl)-ethers of 9α-halo-16-methyl-20-keto-21-desoxy steroids by 17-acylation and 21-acetoxylation, and subsequently by selective removal of the 11β-protective group by hydrolysis with dilute sodium bicarbonate solution or by selective solvolysis with silica gel. Furthermore, this patent described for the first time the selective hydrolysis at 21 of an 11β-trihaloacetate-17,21-diester.

Thus, the prior art processes can be divided into three groups:
(a) Direct esterification of the 17α-hydroxy group without protecting the 11β-hydroxy, such as described in British Pat. Nos. 737,291 and 1,070,751.
(b) Direct esterification of the 17α-hydroxy group, having previously protected the 11β-hydroxy and 21-hydroxy, if present, followed by selective removal of the 11β-protection (British Pat. Nos. 1,097,165, 1,227,992 and U.S. Pat. No. 4,024,131), and subsequent hydrolysis at 21 to prepare the 17α-monoesters (British Pat. Nos. 1,047,518, 1,097,164, 1,227,992, and U.S. Pat. No. 4,024,131).
(c) Preparation of the cyclic 17α,21-orthodiesters, followed by hydrolysis to yield the 17α-monoesters (Belgian Pat. Nos. 618,831, 619,180, and British Pat. Nos. 1043347 and 1047518).

The processes in group (a), esterify concomitantly the 11β-hydroxy group either completely or partially, thus they are no longer industrially useful to prepare 17α-monoesters with an acceptable yield, as no process is known to remove selectively an 11β-ester group of an 11β,17α-diester or of an 11β,17α,21-triester, excepting the 11β-di- or trihalo acetate or a few other specific 11β-ether protecting groups.

The processes in group (b) afford the 11β-protected-17α-mono-21-desoxy and 11β-protected 17α,21-diesters in good yield, as well as processes for removal of the 11β-protection similarly with a good yield. Consequently, the 17α,21-diesters are obtained in a satisfactory manner. However, the removal of the 21-ester group is not sufficiently selective, yielding an impure 17α-ester mixed with a number of by-products. Consequently, the yields are relatively low when preparing 17α-monoesters in pure state. Finally, according to the prior art literature, in group (c) the preparation of the cyclic 17α,21-orthodiesters proceeds usually in good yield without the necessity to protect the 11β-hydroxy group. The acid hydrolysis of these cyclic orthodiesters, however, is not sufficiently selective and is very sensitive to the reaction conditions. It yields, besides the 17α-monoester, 21-monoester and free 11β,17α,21-triol.

In the prior art using direct 17α-acylation of an 11β-protected 21-ester, the 11β-protection is the one which is removed first, thus preparing the 17α,21-diesters, which are subsequently hydrolysed by oncentrated aqueous perchloric acid.

The present invention is based on the discovery that:

(a) When applying acid solvolysis to 17α,21-diesters or to 11β-trifluoroacetate-17α,21-diesters under strictly anhydrous conditions, in contrast to the use of prior art aqueous acids, the selectivity increases unexpectedly and no 21-monoester and no 11β,17α,21-triol, or only small amounts are formed, and yields are increased.

(b) The presence of the 11β-trifluoroacetate group stabilises the 17α-ester group, and it prevents the isomerisation of the 17α-monoester into the 21-monoester even under mild alkaline conditions, which is absolutely unexpected and is of primary importance.

According to the present invention, selective sodium methoxide solvolysis at 11 of 11β-trifluoroacetate-17α,21-diesters of corticosteroids yield the respective 17α,21-diesters in stoichiometric yields of about 93–94%. These latter compounds, according to the present invention, can be solvolysed again at 21, under strictly anhydrous conditions with increased yields and higher selectivities than the prior art processes.

Another feature of the present invention is that 11β-trifluoroacetate-17α,21-diesters of a 20-keto steroid can be solvolysed at 21, under anhydrous conditions, with high selectivity and yield, into 11β-trifluoroacetate-17α-monoesters, and these latter compounds can be solvolysed again with high selectivity into the desired 17α-monoesters.

One of the most important inventive features of the present process lies in the mere fact that the 21- and 11-ester groups are removed under strictly anhydrous conditions and this represents a drastic and unexpected improvement in yield and purity over prior art. In fact, when removing the 11β-trifluoroacetate group by solvolysis is presence of catalytic amounts of sodium methoxide and subsequently the 21-acetate group by solvolysis catalysed by an anhydrous strong acid from the 16β-methyl-9α-fluoroprednisolone 11β-trifluoroacetate-17α-valerate 21-acetate, the desired 17α-monoester is obtained, having a purity of 97.8% with an overall yield of 90%.

One other important feature of the present invention is that this pathway can be reversed, thus, one solvolyses selectively first the 21-ester group, and then the 11β-protection.

In contrast, taking the best yielding steps of the prior art to solvolyse an 11β-trifluoroacetate-17α-valerate 21-acetate at 11β-by sodium benzoate (British Pat. No. 1,097,164, Example 5), recrystallised from acetone hexane followed by perchloric acid hydrolysis at 21 (British Pat. No. 1,097,164, Example 10), the overall stoichiometric yield is 58.8%, the purity being 89.3%.

Thus, the present invention overcomes the shortcomings of the prior art processes in that the 17α-monoesters are obtained in much higher purity and with better yields.

The starting materials are 17α,21-diesters, 11β-trifluoroacetate-17α,21-diesters of a 20-keto steroid or 11β-trifluoroacetate-17α-esters of a 20-keto-21-desoxy steroid.

The starting materials are easily obtainable according to the prior art processes. An 11β,17α,21-triol or 11β,17α-diol,21-ester of a 20-keto steroid is selectively trifluoroacetylated at 11β-by applying the processes of Reichstein (U.S. Pat. No. 2,800,489) and then acylated directly at 17α- when the 21-hydroxy is already esterified or diacylated simultaneously at 17α,21- when the 21-hydroxy is free by the process of Huang-Minlon (British Pat. No. 737,291).

Furthermore, the 11β-trifluoroacetate-17α,21-diesters and 17α,21-diesters can be advantageously prepared by the process described in U.S. Pat. No. 4,024,131 via the 21-iodo derivatives, or a chemically acceptable recombination of the reaction steps therein described.

The selective solvolysis at 11 is carried out in an absolute lower alcohol, preferably methanol, in the presence of small amounts of sodium methoxide, followed by precipitation in ice cold water. The purity of the crude 17α,21-diesters is about 99%.

A most unexpected and surprising effect of the present invention is that the 11β-trifluoroacetate group is removed without or with very little further reaction, in spite of the alkaline conditions. In contrast, when applying methanolic sodium methoxide in the same proportion to 17α,21-diesters, one obtains a mixture which contains mainly the 21-monoester (89.3%) plus some starting material (2.9%), 17α-monoester (3.0%) and 17α,21-diol (4.8%).

The reaction medium is methanol or ethanol or a mixture of both, the quantity of sodium methoxide is 0.05 to 0.6 mole for each mole of 11β-trifluoroacetate 17α,21-diester, and 0.05 to 0.25 for each mole of 11β-trifluoroacetate-17α-monoester, the reaction time being a few minutes and the temperature being comprised between 0° C. and room temperature, preferably at +10° C. When the reaction is finished, it is acidified with 50% aqueous acetic acid and precipitated by adding ice cold water.

According to the present invention, the 17α,21-diester thus obtained is then selectively solvolysed at 21, without further purification. This is carried out in an absolute lower alcohol, preferably methanol, eventually mixed with another solvent inert in the reaction, in the presence of a strong anhydrous acid such as anhydrous perchloric acid or anhydrous para-toluenesulphonic acid.

A practical way to prepare the anhydrous perchloric acid is to mix a methanolic solution of magnesium perchlorate with an ethanolic solution of hydrogen chloride in stoichiometric proportions under anhydrous conditions.

The reaction temperature is between −20° to +30° C. and the reaction time is between a few hours and about 350 hours. The end of the reaction can be easily controlled by thin-layer chromatography.

Once the solvolysis is complete at 21, the 17α-monoester is isolated by conventional means, preferably by precipitating with ice cold water. The crude product thus obtained usually contains very small amounts of starting material, 21-monoester and free 11β,17α,21-triol, in total less than 3%. This value is within the specification of the various pharmacopoeias for foreign steroid content, therefore further purification is not essential. However, it can be further purified by conventional processes, such as recrystallisation from a suitable solvent by adding a non-solvent, i.e. acetone/hexane, or from a hot solvent in which the solubility decreases drastically upon cooling, i.e. methanol.

The stoichiometric step yield for the removal of the 21-ester group is about 95 to 98% on the product as it is.

In contrast, the removal of the 21-ester group from a 17α,21-diester of a 20-keto steroid with the aqueous perchloric hydrolysis of the prior art usually gives lower yields, i.e. 80–85% on the product as it is and poorer selectivity, i.e. 10–20% impurities. In Table I, the yields and purities of the crude reaction products given by British Pat. Nos. 1,047,518 and 1,097,164 are compared with those of the present invention. The increase of stoichiometric yield in the removal of the 21-ester group in the present process is of the order of 20–25%.

An alternative procedure starting with the 11β-trifluoroacetate-17α,21-diester of a corticosteroid is the reversal of the two steps, and this forms another inventive feature of the present process.

Thus, the selective solvolysis at 21 is carried out in an absolute lower alcohol, preferably methaol, eventually mixed with another solvent inert in the reaction, in the presence of a strong anhydrous acid such as anhydrous perchloric acid, hydrogen chloride in methanol or ethanol, anhydrous methanesulphonic acid or anhydrous para-toluenesulphonic acid.

The reaction temperature is between $-20°$ C. to $+30°$ C. and the reaction time is between a few hours and about 250 hours. The end of the reaction can be easily controlled by thin-layer chromatography.

Once the solvolysis is completed at 21, the 11β-trifluoroacetate 17α-ester is isolated by conventional methods, preferably by precipitating with ice cold water. The crude product thus obtained usually contains 0.3 to 1.0% of 17α-monoester. Since this is the desired final product, it does not represent an undesirable by-product. Free 11β,17α,21-triol is co-produced in the amount of 0.1 to 0.4%, which does not intefere in the next step. This solvolysis at 21 also produces some unidentified foreign steroids, detectable by high pressure liquid-liquid chromatography, which are easily eliminated together with some unreacted starting material. The crude 11β-trifluoroacetate-17α-monoesters are purified by conventional methods, such as recrystallisation or by dissolving them in di-methylformamide or tetrahydrofuran containing the carboxylic acid which esterifies the 17α-hydroxy group and methanesulphonic acid or para-toluenesulphonic acid under good stirring, filtering the solution and crystallising by adding it to ice water or by adding aqueous methanol. The stoichiometric step yield for the removal of the 21-ester group is about 92 to 96% on the product as it is, no 17α,21-diester or 21-monoester being detectable by high pressure liquid-liquid chromatography at a sensitivity level of 0.1%.

According to the present invention, the 11β-trifluoroacetate-17α-ester thus obtained is then solvolysed in methanol in the presence of small amounts of sodium methoxide under anhydrous conditions, followed by precipitation with ice cold water. The purity of the crude 17α-monoesters is above 97%, in contrast to the 80–90% purity of the prior art 17α-monoester obtained from hydrolysis of the 17α,21-diester in presence of aqueous perchloric acid. The same process is applicable to the equivalent 21-desoxy series.

The stabilising effect of the 11β-trifluoroacetate on the 17α-substituent is further demonstrated in that 11β-trifluoroacetate-17α,21-orthodiesters can be successfully solvolysed in presence of sodium methoxide simultaneously at 11β- and at 21, affording the 17α-monoester as the major product. Under the same conditions, the 11β-hydroxy-17α,21-orthodiesters do not react.

The quantity of sodium methoxide is 0.05 to 0.15 moles for each mole of 11β-trifluoroacetate-17α, 21-cyclic orthodiesters and the reaction is performed in methanol or ethanol or in a mixture of both at a temperature comprised between $-20°$ and $+30°$ C.

The 17α-monoesters of corticosteriods exert, as known, a high topical anti-inflammatory activity, and the most frequent forms of formulations are creams and ointments. It has been found that these formulations of the 17-esters of corticosteroids when prepared according to the currently used methods are usually unstable and slowly undergo isomerisation, i.e. the 17-ester partially rearranges into the 21-ester. The present invention provides also a formulation to prepare a cream having a good stability where no 21-ester is detectable at a sensitivity level of 0.1% after 24 months at room temperature, as described in Example 22.

In view of the fact that the concentration of topical formulations is low, from about 0.05 to 0.12%, it is advantageous to prepare a microcrystalline product.

According to the present invention, the 17α-monoesters are dissolved in about twice the volume of di-methylformamide, which is acidified with the acid forming the 17-ester grouping, in presence of pyridine or of a strong acid so as to avoid 21-isomerisation. The solution thus obtained is filtered and added dropwise to about 10 volumes of ice cold filtered water under efficient stirring. The cyrstals are filtered, washed and dried. About 85% of the crystals are smaller than 10μ. This procedure can be advantageously combined with simultaneous decoloration of the product by adding 2 to 5% of active carbon to the solution and stirring the product for 1 hour to overnight at maximum before filtration. In the case where active carbon is added, the stabilisation is preferably effected with carboxylic acid corresponding to the 17-ester function in the amount of 0.1 to 1.0%, calculated on the amount of dimethyl-formamide, plus a strong acid, preferably para-toluenesulphonic acid or methanesulphonic acid.

When using the pyridine addition salt of the corresponding carboxylic acid, it should preferably be prepared "in situ" and under completely anhydrous conditions.

The thus obtained microcrystalline product, when formulated, will assure an equal homogeneous distribution in creams and ointments.

The present invention is applicable to the known 11β,17α-dihydroxy- and 11β,17α,21-trihydroxy 20-keto steroids, more particularly to 16α-methyl-9α-fluoro-prednisolone and 16β-methyl-9α-fluoroprednisolone.

The Examples appearing hereafter serve to illustrate the present invention, without however limiting its scope.

EXAMPLE 1

Preparation of BETAMETHASONE 11-TRIFLUOROACETATE 17-VALERATE

Methanesulphonic acid (1.0 ml) was added to a suspension of 9α-fluoro-11β,17α,21-trihydroxy-16β-methylpregna-1,4-diene-3,20-dione 11-trifluoroacetate 17-valerate 21-acetate (20.0 g) in absolute methanol (60 ml), which was then stirred at 18° C. for 24.5 hours, then at 25° C. for 2.75 hours, with the exclusion of moisture. The product was precipitated by pouring into ice cold water (750 ml), then filtered, washed with water and dried at 40°–50° C., to yield 17.98 g. By chromatographic comparison with an authentic sample, the major product was shown to be betamethasone 11-trifluoroacetate 17-valerate, with the following analytical values:

mpt 158°–9° C.

I.R. (nujol mull) Principal peaks at 3,400, 2,900, 2,840, 1,780, 1,720, 1,660, 1,630 cm$^{-1}$ U.V. $E_{1\ cm}^{1\%}$ 277 at 238-9 nm in methanol. The minor impurity was shown to be betamethasone 17-valerate, which is the required product in the following reaction in the series.

EXAMPLE 2

Preparation of BETAMETHASONE 11-TRIFLUOROACETATE 17-VALERATE

9α-Fluoro-11β,17α, 21-trihydroxy-16β-methylpregna-1,4-diene-3,20-dione 11-trifluoroacetate 17-valerate 21-acetate (10.0 g) was added to a mixture of absolute methanol (25 ml), ethanolic hydrogen chloride solution (11.3 ml; 16.22% w/v) and anhydrous magnesium perchlorate (5.55 g). The last two reagents will produce anhydrous perchloric acid (5.00 g) in situ. The mixture, which was protected from moisture, was stirred at 10° C. for 90 hours, and then poured into ice cold water (300 ml). The precipitated product was filtered, washed with water and dried at 40°-50° C., to yield 8.91 g. The major product was identified as betamethasone 11-trifluoroacetate 17-valerate by chromatographic comparison with an authentic sample. The analytical values were:

mpt 155°-8° C.

I.R. (nujol mull) Principal peaks at 3,400, 2,900, 2,850, 1,780, 1,720, 1,670, 1,630 cm$^{-1}$ U.V. $E_{1\ cm}^{1\%}$ 274 at 238-9 nm in methanol.

The minor impurity was shown to be betamethasone 17-valerate, which is the required product in the following reaction in the series.

EXAMPLE 3

Preparation of BETAMETHASONE 11-TRIFLUOROACETATE 17-VALERATE p-Toluenesulphonic acid (2.50 g, previously dried at 130° C. for 16 hours) was added to absolute methanol (15 ml), followed by 9α-fluoro-11β,17α,21-trihydroxy-16β-methylpregna-1,4-diene-3,20-dione 11-trifluoroacetate 17-valerate 21-acetate (5.00 g). The mixture, which was protected from moisture by a calcium chloride drying tube, was stirred at 10° C. for 72 hours, after which it was poured into ice cold water (300 ml). The precipitated product was filtered, washed with water and dried at 40°-50° C. to yield 4.31 g. The major product was identified as betamethasone 11-trifluoroacetate 17-valerate by comparison with an authentic sample by T.L.C. The analytical values were:

m.p.t. 156°-9° C.

I.R. (nujol mull) Principal peaks at 3600, 2900 2830, 1760, 1725, 1650 cm$^{-1}$ U.V. $E_{1\ cm}^{1\%}$ 275 at 238-9 nm in methanol.

The minor impurity was found to be betamethasone 17-valerate, the final product of the next reaction in the series.

2 gr. of the 11-trifluoroacetae 17-valerate above obtained was dissolved in 4 ml tetrahydrofuran containing 2% valeric acid, 2.5% p-toluenesulfonic acid, under stirring and filtered. Then the solution was diluted with 9.6 ml of methanol followed immediately by the addition of 2.4 ml of water under good stirring. The crystals thus formed were filtered, washed and dried. The filtrate was diluted with water and the precipitate formed was filtered, dried and purified by repeating the above process, yielding a second crop of suitable purity to be used in the next step. Overall purification yield 93.1%.

EXAMPLE 4

Preparation of BETAMETHASONE 11-TRIFLUOROACETATE 17-VALERATE

9α-Fluoro-11β,17α,21-trihydroxy-16β-methylpregna-1,4-diene,3,20-dione 11-trifluoroacetae 17-valerate 21-acetate (1.50 g) was dissolved in a mixture of absolute methanol (9 ml) and ethanolic hydrogen chloride (17.78% w/v, 3.0 ml) and the mixture was stirred at 23.5° C. for 8 hours. After precipitation in ice cold water (100 ml), the product was collected by filtration, washed with water, dried at 40°-50° C., to yield 1.32 g. It was identified as betamethasone 11-trifluoroacetate 17-valerate by chromatographic comparison with an authentic sample and by the following analysis:

mpt 150°-152° C.

I.R. (nujol mull) Principal peaks at 3,400, 1,770, 1,720, 1,660, 1,635, 1,610 cm$^{-1}$ U.V. $E_{1\ cm}^{1\%}$ 273 at 238-9 nm in methanol.

EXAMPLE 5

Preparation of DEXAMETHASONE 11-TRIFLUOROACETATE 17-VALERATE

Methanesulphonic acid (3.0 ml) was added to a mixture of 9α-fluoro-11β,17α,21-trihydroxy-16α-methylpregna-1,4-diene-3,20-dione 11-trifluoroacetae 17-valerate 21-acetate (10.0 g) in absolute methanol (50 ml), which was then stood at −20° C. for 65 hours, with the exclusion of moisture. The product was precipitated by pouring into ice cold water (500 ml), then filtered, washed with water, dried at 40°-50° C. to yield 8.87 g. The product was shown to be dexamethasone 11-trifluoroacetae 17-valerate by chromatographic comparison with an authentic sample and by the following analytical values:

I.R. (nujol mull) Principal peaks at 3,400, 2,920, 2,850, 1,790, 1,740, 1,670, 1,630, 1,610(sh) cm$^{-1}$ U.V. $E_{1\ cm}^{1\%}$ 271 at 236 nm in methanol One minor impurity was present and was shown to be dexamethasone 17-valerate which is the final product of the next transformation of this series.

EXAMPLE 6

Preparation of DEXAMETHASONE 11-TRIFLUOROACETATE 17-VALERATE p-Toluenesulphonic acid (1.0 g, previously dried at 130° C. for 16 hours) was added to a solution of 9α-fluoro-11β,17α,21-trihydroxy-16α-methylpregna-1,4-diene-3,20-dione 11-trifluoroacetate 17-valerate 21-acetate (2.0 g) in absolute methanol (10 ml). The mixture, which was protected from moisture by a calcium chloride drying tube, was stood at −19° C. for 8 days. The product was precipitated by pouring into ice cold water (100 ml), collected by filtration, washed with water, dried at 40°-50° C. to yield 1.77 g. The major product was shown to be dexamethasone 11-trifluoroacetate 17-valerate by chromatographic comparison with an authentic sample and by the following analysis:

mpt 108°-110° C.

I.R. (nujol mull) Principal peaks at 3,390, 1,770, 1,720, 1,660, 1,630 cm$^{-1}$ U.V. $E_{1\ cm}^{1\%}$ 275 at 236-8 nm in methanol One minor impurity was present in the product and was shown to be dexamethasone 17-valerate, the required product in the next reaction of the series.

EXAMPLE 7

Preparation of DEXAMETHASONE 11-TRIFLUOROACETATE 17-VALERATE

9α-Fluoro-11β,17α,21-trihydroxy-16α-methylpregna-1,4-diene-3,20-dione 11-trifluoroacetate 17-valerate 21-acetate (2.00 g) was dissolved in absolute methanol (10 ml) and then cooled to −20° C. Anhydrous magnesium perchlorate (1.0 g) and ethanolic hydrogen chloride (17.15%, 1.72 ml), which will produce anhydrous perchloric acid (813 mg) in situ, were then added and the mixture stood at −20° C. for 15 days. The product was precipitated in ice cold water (100 ml), collected by filteration, washed with water, dried at 40°–50° C., to yield 1.8 g. It was identified as dexamethasone 11-trifluoroacetate 17-valerate by chromatographic comparison with an authentic sample and by the following analysis:

mpt 120° C.

I.R. (nujol mull) Principal peaks at 3,350, 1,750, 1,720, 1,660, 1,630, 1,610 cm$^{-1}$ U.V. $E_{1\ cm}^{1\%}$ 268 at 235–6 nm in methanol.

EXAMPLE 8

Preparation of DEXAMETHASONE 11-TRIFLUOROACETAE 17-VALERATE

A mixture of 9α-fluoro-11β,17α,21-trihydroxy-16α-methylpregna-1,4-diene-3,20-dione 11-trifluoroacetate 17-valerate 21-acetate (2.00 g) and ethanolic hydrogen chloride 12.82% w/v, 4 ml) in absolute methanol (10 ml) was stirred at 21°–2° C. for 7 hours. The product was precipitated in ice cold water (100 ml), filtered, washed with water, dried at 40°–50° C. to yield 1.71 g. This was identified as dexamethasone 11-trifluoroacetae 17-valerate by chromatographic comparison with an authenic sample and by the following analysis:

mpt 112°–5° C.

I.R. (nujol mull) Principal peaks at 3,350, 1,770, 1,720, 1,660, 1,630, 1,600 cm$^{-1}$ U.V. $E_{1\ cm}^{1\%}$ 261 at 235–7 nm in methanol.

EXAMPLE 9

Preparation of BETAMETHASONE 17-VALERATE

A1. According to the present invention, a mixture of 9α-fluoro-11β,17α,21-trihydroxy-16β-methylpregna-1,4-diene-3,20-dione 17-valerate 21-acetate (2.00 g), p-toluene sulphonic acid (previously dried at 130° C. for 16 hours, 0.10 g) in absolute methanol (6 ml) was stirred at 10° C. for 8 days. After pouring into ice cold water (60 ml), the product was filtered, washed with water, dried at 40°–50° C., to yield 1.80 g. It was identified as betamethasone 17-valerate by chromatographic comparison with an authentic sample and by the following analysis:

I.R. (nujol mull) Principal peaks at 3,350, 1,725, 1,710 (sh), 1,660, 1,600 cm$^{-1}$ U.V. $E_{1\ cm}^{1\%}$ 319 at 239 nm in absolute alcohol.

A2. According to the present invention, 9α-fluoro-11β,17α,21-trihydroxy-16β-methylpregna-1,4-diene-3,20-dione 17-valerate 21-acetate (2.00 g) was added to absolute methanol (6 ml), followed by anhydrous magnesium perchlorate (0.11 g) and ethanolic hydrogen chloride (17.15% w/v, 0.19 ml). The last two reagents will produce anhydrous perchloric acid (90 mg) in situ. The mixture was stirred at 10° C. for 14 days, then poured into ice cold water (60 ml). The precipitate was filtered, washed with water, dried at 40°–50° C. to yield 1.75 g. It was shown to be betamethasone 17-valerate by chromatographic comparison with an authentic sample and by the following analysis:

mpt 184°–90° C.

I.R. (nujol mull) Principal peaks at 3,250, 1,725, 1,710 (sh), 1,660, 1,600 cm$^{-1}$ U.V. $E_{1\ cm}^{1\%}$ 317 at 238–9 nm in absolute alcohol.

B1. Comparative preparation according to British patent No. 1,047,518 (Example 11):

9α-Fluoro-11β,17α,21-trihydroxy-16β-methylpregna-1,4-diene-3,20-dione 17-valerate 21-acetate (10.00 g) was dissolved in methanol (556 ml) and aqueous perchloric acid (70%, 38.9 ml) was added slowly. The mixture was stood at room temperature for 5 hours, and then precipitated in ice cold water (5550 ml). The product was filtered, washed with water until the washings were neutral, dried at 40°–50° C. to yield 7.80 g. By thin layer chromatography, the product consisted mainly of betamethasone 17-valerate, plus starting material and betamethasone 21-valerate. The analytical values were as follows:

mpt 180°–5° C.

I.R. (nujol mull) Principal peaks at 3,400, 1,735, 1,660, 1,620, 1600(sh) cm$^{-1}$ U.V. $E_{1\ cm}^{1\%}$ 325 at 239 nm in methanol.

B2. Comparative preparation according to British patent No. 1,097,164 (Example 10):

9α-Fluoro-11β,17α,21-trihydroxy-16β-methylpregna-1,4-diene-3,20-dione 17-valerate 21-acetate (10.00 g) was dissolved in methanol (680 ml) and the solution cooled to 0° C. Aqueous perchloric acid (70%, 70 ml) was added slowly and the mixture maintained at 0° C. with stirring for 48 hours. The product was precipitated in ice cold water (7000 ml), filtered, washed with water until the washings were neutral, dried at 40°–50° C., to give 7.56 g. The major product was shown to be betamethasone 17-valerate by thin layer chromatography together with some starting material and betamethasone 21-valerate. The analytical values were as follows:

mpt. 185° C.

I.R. (nujol mull) Principal peaks at 3,400, 1,735, 1,720(sh), 1,660, 1,620, 1,600(sh) cm$^{-1}$ U.V. $E_{1\ cm}^{1\%}$ 329 at 238 nm in methanol.

The impurities of all the compounds obtained in this Example have been determined by high performance liquid chromatography and the results are compared in Table I.

EXAMPLE 10

Preparation of DEXAMETHASONE 17-VALERATE

A mixture of 9α-fluoro-11β,17α,21-trihydroxy-16α-methylpregna-1,4-diene-3,20-dione 17-valerate 21-acetate (2.00 g), p-toluenesolphonic acid (previously dried at 130° C. for 16 hours, 1.00 g) in absolute methanol (10 ml) was stood at −20° C. for 9 days. The product was precipitated in ice cold water (100 ml), collected by filtration, washed with water, dried at 40°–50° C. to yield 1.58 g. This was identified as dexamethasone 17-valerate by chromatographic comparison with an authentic sample and by the following analysis:

mpt 193°–6° C.

I.R. (nujol mull) Principal peaks at 3,340, 1,710, 1,645, 1,600 cm$^{-1}$

U.V. $E_{1\ cm}^{1\%}$ 318 at 239 nm in methanol

EXAMPLE 11

Preparation of DEXAMETHASONE 17-VALERATE

A solution of 9α-fluoro-11β,17α,21-trihydroxy-16α-methylpregna-1,4-diene-3,20-dione 17-valerate 21-acetate (1.50 g), absolute methanol (7.5 ml), anhydrous magnesium perchlorate (0.59 g) and ethanolic hydrogen chloride (1.15 ml) was stood at −20° C. for 16 days, with the exclusion of moisture. The last two reagents will form anhydrous perchloric acid (531 mg) in situ. The product was precipitated in ice cold water (100 ml) filtered, washed with water, dried at 40°-50° C. to yield 1.21 g. It was identified as dexamethasone 17-valerate by chromatographic comparison with an authentic sample and by the following analysis:

I.R. (nujol mull) Principal peaks at 3,400, 1,725, 1,655, 1,610 cm$^{-1}$

U.V. $E_{1\ cm}^{1\%}$ 325 at 239 nm in methanol.

EXAMPLE 12

Preparation of DEXAMETHASONE 17-VALERATE

A mixture of 9α-fluoro-11β,17α,21-trihydroxy-16α-methylpregna-1,4-diene-3,20-dione 17-valerate 21-acetate (2.00 g), absolute methanol (10 ml), anhydrous magnesium perchlorate (0.78 g) and ethanolic hydrogen chloride (1.36 ml) was stood at −20° C. for 13 days. The last two reagents will produce anhydrous perchloric acid (642 mg) in situ. The product was precipitated in ice cold water (100 ml), filtered, washed with water, dried at 40°-50° C. to yield 1.72 g. It was shown to be dexamethasone 17-valerate by chromatographic comparison with an authentic sample and by the following analysis:

I.R. (nujol mull) Principal peaks at 3,350, 1,720, 1,655, 1,610 cm$^{-1}$

U.V. $E_{1\ cm}^{1\%}$ 315 at 237-9 nm in methanol.

EXAMPLE 13

Preparation of BETAMETHASONE 17-VALERATE 21-ACETATE

A. According to the present invention, 9α-fluoro-11β,17α,21-trihydroxy-16β-methylpregna-1,4-diene-3,20-dione 11-trifluoroacetate 17-valerate 21-acetate (10.00 g) was dissolved in absolute methanol (60 ml) and the solution cooled to 10° C. Methanolic sodium methoxide (1.056 N, 1.0 ml) was added and the mixture stirred at 10° C. for 10 minutes. After neutralisation with 50% aqueous acetic acid, the product was precipitated in ice cold water (1000 ml). It was collected by filtration, washed with water, dried at 40°-50° C. to yield 8.03 g. Chromatographic comparison with an authentic sample showed the product to be betamethasone 17-valerate 21-acetate, as did the following analysis:

mpt. 203°-207° C.

I.R. (nujol mull) Principal peaks at 3,450, 1,750, 1,735, 1,660, 1,625, 1,600 cm$^{-1}$ U.V. $E_{1\ cm}^{1\%}$ 297 at 238 nm in methanol.

B. Comparative preparation according to British patent No. 1,097,164 (Example 5)

A suspension of sodium benzoate (100.0 g), 9α-fluoro-11β,17α,21-trihydroxy-16β-methylpregna-1,4-diene-3,20-dione 11-trifluoroacetate 17-valerate 21-acetate (10.00 g) in ethanol (450 ml) was energetically stirred for one hour at 20° C. After precipitation in ice cold water (4500 ml), the product was filtered, washed with water, dried at 40°-50° C. to yield 8.60 g. The product was shown by thin layer chromatography to be a mixture of starting material and betamethasone 17-valerate 21-acetate. The analytical values were as follows:

mpt. 185°-192° C.

I.R. (nujol mull) Principal peaks at 1,800, 1,750, 1,735, 1,660, 1,625, 1,600 cm$^{-1}$ U.V. $E_{1\ cm}^{1\%}$ 286 at 238-239 nm in methanol.

The impurities of all the compounds obtained in this Example have been determined by high performance liquid chromatography and the results are compared in Table I.

5 gr of the crude product obtained above was dissolved in 25 ml acetone, filtered and crystallised by adding 250 ml hexane. The crystals thus formed were filtered, washed and dried. The filtrate was then evaporated under reduced pressure. The residue was dissolved in the minimum amount of acetone (12 ml) then 120 ml of hexane were added. The crystals of this second crop were of suitable purity for use in the next step. The overall purification yield was 70.1%.

EXAMPLE 14

Preparation of BETAMETHASONE 17,21-DIACETATE

To a suspension of 9α-fluoro-11β,17α,21-trihydroxy-16β-methylpregna-1,4-diene-3,20-dione 11-trifluoroacetate 17,21-diacetate (2.00 g) in absolute methanol (12 ml) was added methanolic sodium methoxide (1.045 N, 0.8 ml). The mixture was stirred for 5 minutes at 10° C., then neutralised with 50% aqueous acetic acid. The product was precipitated in ice cold water (120 ml), filtered, washed with water, dried at 40°-50° C. to yield 1.58 g. It was identified as betamethasone 17,21-diacetate by chromatographic comparison with an authentic sample and by the following analysis:

mpt. 155° C.

I.R. (nujol mull) Principal peaks at 3,600, 3,390, 1,750, 1,725, 1,660, 1,625, 1,600 cm$^{-1}$ U.V. $E_{1\ cm}^{1\%}$ 316 at 238-239 nm in methanol.

EXAMPLE 15

Preparation of DEXAMETHASONE 17-VALERATE 21-ACETATE

9α-Fluoro-11β,17α,21-trihydroxy-16α-methylpregna-1,4-diene-3,20-dione 11-trifluoroacetate 17-valerate 21-acetate (2.00 g) was dissolved in absolute methanol (12 ml). After addition of methanolic sodium methoxide (1.051 N, 1.6 ml) the mixture was stirred at room temperature for 30 minutes, when it was neutralised with 50% aqueous acetic acid. The product was precipitated in ice cold water (200 ml), filtered, washed with water, dried at 40°-50° C. to yield 1.40 g. It was shown to be dexamethasone 17-valerate 21-acetate by chromatographic comparison with an authentic sample and by the following analysis:

mpt. 129°-132° C.

I.R. (nujol mull) Principal peaks at 3,370, 1,760(sh), 1,725, 1,660, 1,620, 1,600 cm$^{-1}$ U.V. $E_{1\ cm}^{1\%}$ 300 at 238-240 nm in methanol.

EXAMPLE 16

Preparation of BETAMETHASONE 17-VALERATE

9α-Fluoro-11β,17α,21-trihydroxy-16β-methylpregna-1,4-diene-3,20-dione 11-trifluoroacetate 17-valerate (50.0 g) was suspended in absolute methanolic (400 ml) and methanol sodium methoxide (1.118 N; 11.8 ml) was added. The mixture was well stirred for 4 minutes at 26° C., during which time it dissolved and then crystallised. After addition of 50% aqueous acetic acid to affect neutralisation, the volume was reduced to 100 ml by concentration under vacuum. The product was precipitated in ice cold water (1,500 ml), collected by filtration, washed with water and dried at 40°-50° C., to yield 40.69 g. The product complied with the Pharmacopoeia specifications including the USP XX HPLC assay. Thus, the stoichiometric yield of betamethasone 17-valerate was 97.8%. The impurities of the compound obtained in this Example have been determined by high performance liquid chromatography and the results are given in Table I.

EXAMPLE 17

Preparation of DEXAMETHASONE 17-VALERATE

9α-Fluoro-11β,17α,21-trihydroxy-16α-methylpregna-1,4-diene-3,20-dione 11-trifluoroacetate 17-valerate (2.50 g) was dissolved in absolute methanol (12.5 ml) and sodium bicarbonate (250 mg) was added. The suspension was stirred for 45 minutes at room temperature, followed by neutralisation with 50% aqueous acetic acid. The product was precipitated by addition to ice cold water (150 ml), collected by filtration, washed with water, dried at 40°-50° C. to yield 2.01 g. The product was identified as dexamethasone 17-valerate by chromatographic comparison with an authentic sample and by the following analysis:

mpt 175°-183° C.

I.R. (nujol mull) Principal peaks at 3,460, 3,350, 1,720, 1,650, 1,610 cm$^{-1}$ U.V. $E_{1\,cm}^{1\%}$ 325 at 237–240 nm in methanol.

EXAMPLE 18

Preparation of DEXAMETHASONE 17-VALERATE

9α-Fluoro-11β,17α,21-trihydroxy-16α-methylpregna-1,4-diene-3,20-dione 11-trifluoroacetate 17-valerate (5.0 g) was dissolved in absolute methanol (30 ml) and methanolic sodium methoxide (1.067 N, 0.5 ml) was added. The mixture was stirred at 10° C. for 20 minutes and then neutralised with 50% aqueous acetic acid. The product was precipitated in ice cold water (300 ml), filtered, washed with water, dried at 40°-50° C. to yield 4.30 g. By chromatographic comparison with an authentic sample, the product was identified as dexamethasone 17-valerate. The analysis was:

mpt. 174°-178° C.

I.R. (nujol mull) Principal peaks at 3,410, 3,310, 1,730, 1,660, 1,620 cm$^{-1}$ U.V. $E_{1\,cm}^{1\%}$ 324 at 239 nm in methanol.

EXAMPLE 19

Preparation of 21-DESOXYBETAMTHASONE 17-VALERATE

Methanolic sodium methoxide (1.004 N, 1.3 ml) was added to a suspension of 9α-fluoro-11β,17α-dihydroxy-16β-methylpregna-1,4-diene-3,20-dione 11-trifluoroacetate 17-valerate (5.00 g) in absolute methanol (80 ml) and the mixture was stirred at 22° C. for 4 minutes. After neutralisation with 50% aqueous acetic acid and concentration under vacuum to 10 ml, the product was precipitated in ice cold water (150 ml), filtered, washed with water, dried at 40°-50° C. to yield 4.05 g. This was identified as 21-desoxybetamethasone 17-valerate by chromatographic comparison with an authentic sample and by the following analysis:

mpt 212°-214° C.

I.R. (nujol mull) Principal peaks at 3,350, 1,720, 1,650, 1,610(sh), 1,590 cm$^{-1}$ U.V. $E_{1\,cm}^{1\%}$ 345 at 239 nm in methanol.

EXAMPLE 20

Preparation of BETAMETHASONE 17-PROPIONATE

9α-Fluoro-11β,17α,21-trihydroxy-16β-methylpregna-1,4-diene-3,20-dione 11-trifluoroacetate 17,21-orthopropionate (1.50 g) was added to a mixture of absolute methanolic (18 ml) and methanol sodium methoxide (1.045 N, 0.15 ml). The mixture was stirred at 21° C. for 1 hour, before being precipitated in ice cold water (180 ml). The yield after filtration, washing with water and drying at 40°-50° C., was 1.10 g. The product was identified as betamethasone 17-propionate by chromatographic comparison with an authentic sample and by the following analysis:

mpt. 232° C.

I.R. (nujol mull) Principal peaks at 3,410, 3,310, 1,720, 1,660, 1,600 cm$^{-1}$ U.V. $E_{1\,cm}^{1\%}$ 356 at 238–239 nm in methanol.

EXAMPLE 21

1 kg. of betamethasone 17β-valerate, obtained according to the process of Example 9A1, is dissolved in 2 lts. of dimethylformamide containing 40 ml. of valeric acid and 50 gr. of anhydrous para-toluenesulphonic acid. Subsequently, 50 gr. of active carbon is added, the mixture is stirred overnight, filtered and poured dropwise over a period of 2 to 3 hours into 10 lts. of ice cold filtered bidistilled water. It is filtered, washed with water and dried at 45° C., yielding 989 gr. of colourless product, the size of 85% of the crystals being below 10μ. The betamethasone valerate thus obtained is specially suitable to prepare topical formulations.

EXAMPLE 22

A water miscible cream of betamethasone 17-valerate is prepared as follows:

Part I—Mix and melt at 70° C. in a water bath:
Cetostearyl alcohol ("Lanette O"$^R$) . . . 18.0%
Cetostearyl alcohol containing approx. 12 moles of ethylene oxide ("Eumulgin B1"$^R$) . . . 1.5%
Cetostearyl alcohol containing approx. 12 moles of ethylene oxide ("Eumulgin B2"$^R$) . . . 1.5%
Caprylic/capric acid triglyceride ("Myritol 318") . . . 10.0%

Part II—Suspend at room temperature:
Betamethasone 17-valerate . . . the equivalent to 0.1% of betamethasone
Glycerol . . . 5%
and ball mill it.

Part III—Dissolve at boiling point:
Methyl p-hydroxybenzoate . . . 0.3%
in
Bidistilled water . . . 63.6%

Cool it to 70° C. and adjust the volume if necessary. Add ⅓ of Part III to Part I with stirring at 70° C., add Part II and finally add the remainder of Part III at 70° C., still under stirring. A jelly starts to set at about 55° C. Continue to stir to ensure a good homogeneity until cooling down to room temperature. The pH will lie between 5 to 5.3.

The tubes filled with this cream show no 21-valerate formation after 24 months by high performance liquid chromatography at a sensitivity level of 0.1%.

TABLE 1

| Starting Material | Process | Example No. | W/W Yield | Stoichio Metric Yield | Percentage of the produced Betamethasone esters found by HPLC | | | | | | Stoichio Metric Yield Of Pure Product |
|---|---|---|---|---|---|---|---|---|---|---|---|
| | | | | | 11-TFA 17-Valerate 21-Acetate | 11-TFA 17-Valerate 21-OH | 11-OH 17-Valerate 21-Acetate | 11-OH 17-OH 21-Valerate | 11-OH 17-Valerate 21-OH | 11-OH 17-OH 21-OH | |
| Betamethasone 17-Valerate 21-Acetate | 70% Perchloric Acid, according to British patent 1,047,518 | 9B1 | 78.0 | 84.9 | — | — | 8.4 | 8.0 | 82.8 | 0.8 | 70.3 |
| Betamethasone 17-Valerate 21-Acetate | 70% Perchloric Acid, according to British patent 1,097,164 | 9B2 | 75.6 | 82.3 | — | — | 3.3 | 6.6 | 89.3 | 0.8 | 73.5 |
| Betamethasone 17-Valerate 21-Acetate | Anhydrous para-Toluene sulphonic Acid | 9A1 | 90.0 | 97.9 | — | — | 3.3 | 0.9 | 94.1 | 1.7 | 92.2 |
| Betamethasone 17-Valerate 21-Acetate | Anhydrous Perchloric Acid | 9A2 | 87.5 | 95.2 | — | — | 0.2 | 0.6 | 97.8 | 1.4 | 93.1 |
| Betamethasone 11-Trifluoroacetate 17-Valerate 21-Acetate | Sodium Benzoate, according to British patent 1,097,164 | 13B1 | 86.0 | 102.0 | 16.8 | 0.2 | 82.9 | 0 | 0.1 | 0 | 84.6 |
| Betamethasone 11-Trifluoroacetate 17-Valerate 21-Acetate | Sodium Methoxide | 13A | 80.3 | 95.3 | 0 | 0.4 | 98.9 | 0 | 0.7 | 0 | 94.2 |
| Betamethasone 11-Trilfuoroacetate 17-Valerate | Sodium Methoxide | 16 | 81.4 | 98.9 | — | 0 | — | 2.8 | 97.2 | 0 | 96.1 |

NOTES:
1. TFA stands for the trifluoroacetate group.
2. The analyses were so performed that products were detectable at the level of 0.1%.
3. At this sensitivity, no other impurities were detected.

We claim:
1. A process for the solvolysis at 11 of an 11β-trihaloacyl-16-methylcorticosteroid to form an ester of the formula

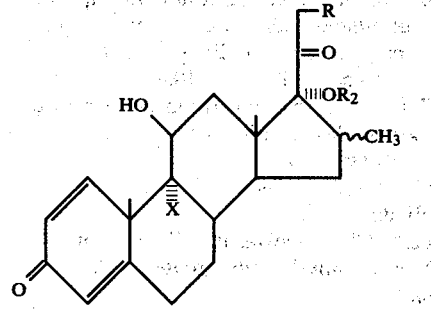

wherein the methyl group is in the 16α- or 16β-position, R is hydrogen or $OR_3$, X is hydrogen or fluorine, $R_2$ is acyl and $R_3$ is a hydrogen or an aliphatic acyl group of 2 to 5 carbon atoms which comprises solvolysing an ester of the formula

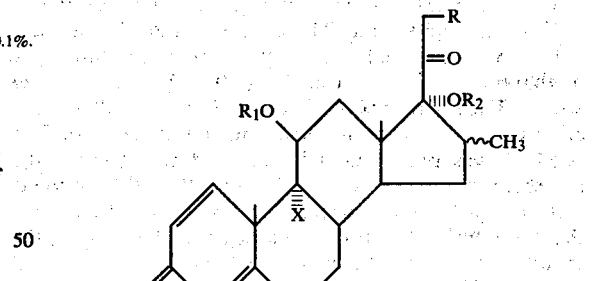

or a cyclic ortho-ester thereof of the formula

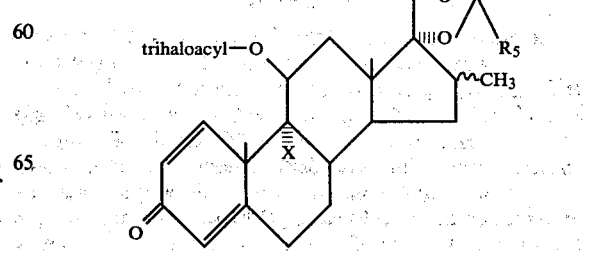

-continued wherein $R_1$ is hydrogen or a trihaloacyl group, $R_4$ is alkyl of 1 to 3 carbon atoms and $R_5$ is alkyl of 1 to 16 carbon atoms, aralkyl of 7 or 8 carbon atoms or phenyl with a catalytic quantity of sodium methoxide in an anhydrous medium.

2. A process according to claim 1, wherein the trihaloacyl group is trifluoroacetate.

3. Process according to claim 1 wherein the anhydrous medium is anhydrous methanol or ethanol in the presence or absence of other solvents insert in the reaction.

4. Process according to claim 1 wherein the ester reactant is a 11,17,21-triester and the amount of sodium methoxide is between 0.05 and 0.6 moles for each mole set as the reactant.

5. Process according to claim 1 wherein the ester reactant is a 11,17-diester and the amount of sodium methoxide is between 0.05 and 0.25 moles for each mole of said ester reactant.

6. Process according to claim 1 wherein said ester reactant is said orthoester and the amount of sodium methoxide is between 0.05 and 0.15 moles for each mole of said orthoester reactant.

7. Process according to claim 1 wherein the R moiety of said ester reactant is $OR_3$ and $R_3$ is said aliphatic acyl group and wherein said 21 ester group is solvosized with a strong acid in an anhydrous medium containing a lower alcohol.

8. Process according to claim 7 wherein said strong acid is selected from the group consisting of p-toluenesulfonic acid, methanesulfonic acid, perchloric acid and hydrogen chloride.

9. Process according to claim 7 wherein the acid solvolysis is effected within the temperature range of $-20°$ C. to $+30°$ C.

* * * * *

UNITED STATES PATENT AND TRADEMARK OFFICE
CERTIFICATE OF CORRECTION

PATENT NO. : 4,343,739         Page 1 of 2
DATED : August 10, 1982
INVENTOR(S) : Ivan Villax, et al It is certified that error appears in the above-identified patent and that said Letters Patent are hereby corrected as shown below:

Column 2, line 66, for "oncentrated" read -- concentrated --.

Column 3, line 36, for "is" read -- in --; line 50, for "acetone hexane" read -- acetone/hexane --.

Column 5, line 12, for "methaol" read -- methanol --; line 29, for "intefere" read -- interfere --.

Column 6, line 24, for "cyrstals" read -- crystals --.

Column 7, line 59, for "trifluoroacetae" read -- trifluoroacetate --.

Column 8, line 7, for "trifluoroacetae" read -- trifluoroacetate --; line 28, for "trifluoroacetae" read -- trifluoroacetate --; line 35, for "trifluoroacetae" read -- trifluoroacetate --.

Column 9, line 26, for "TRIFLUOROACETAE" read -- TRIFLUOROACETATE --; line 30, for "12.82%" read -- (12.82% --; line 34, for "trifluoroacetae" read -- trifluoroacetate --; line 36, for "authenic" read -- authentic --.

Column 13, line 1, for "methanolic" read -- methanol --; line 2, for "methanol" read -- methanolic --;

UNITED STATES PATENT AND TRADEMARK OFFICE
CERTIFICATE OF CORRECTION

PATENT NO. : 4,343,739

DATED : August 10, 1982

INVENTOR(S) : Ivan Villax, et al

Page 2 of 2

It is certified that error appears in the above-identified patent and that said Letters Patent are hereby corrected as shown below:

line 58, for "DESOXYBETAMTHASONE" read -- DESOXYBETAMETHASONE --.

Column 14, line 16, for "methanolic" read -- methanol -- and for "methanol" read -- methanolic --; line 30, for "17$\beta$-valerate" read -- 17$\alpha$-valerate --; line 51, for "12" read -- 20 --.

Column 18, line 9, for "solvosized" read -- solvolysed --.

Signed and Sealed this

Twenty-first Day of December 1982

[SEAL]

Attest:

GERALD J. MOSSINGHOFF

Attesting Officer

Commissioner of Patents and Trademarks